US009428427B2

(12) United States Patent
Goris et al.

(10) Patent No.: US 9,428,427 B2
(45) Date of Patent: Aug. 30, 2016

(54) PROCESS FOR NITRILE REMOVAL FROM HYDROCARBON FEEDS

(75) Inventors: Hans K. T. Goris, Zaventem (BE); Machteld M. W. Mertens, Flemington, NJ (US); Luc R. M. Martens, Meise (BE)

(73) Assignee: ExxonMobil Chemical Patents Inc., Baytown, TX (US)

( * ) Notice: Subject to any disclaimer, the term of this patent is extended or adjusted under 35 U.S.C. 154(b) by 330 days.

(21) Appl. No.: 14/233,183

(22) PCT Filed: Jun. 14, 2012

(86) PCT No.: PCT/EP2012/061364
§ 371 (c)(1),
(2), (4) Date: Jun. 26, 2014

(87) PCT Pub. No.: WO2013/013884
PCT Pub. Date: Jan. 31, 2013

(65) Prior Publication Data
US 2015/0073193 A1 Mar. 12, 2015

(30) Foreign Application Priority Data
Jul. 25, 2011 (EP) ..................... 11175232

(51) Int. Cl.
| | |
|---|---|
| *C07C 2/02* | (2006.01) |
| *C07C 7/12* | (2006.01) |
| *C07C 7/00* | (2006.01) |
| *C07C 7/148* | (2006.01) |
| *B01J 20/06* | (2006.01) |
| *B01J 20/08* | (2006.01) |
| *B01J 20/12* | (2006.01) |
| *B01J 20/18* | (2006.01) |
| *B01J 20/20* | (2006.01) |
| *B01J 21/04* | (2006.01) |
| *B01J 29/70* | (2006.01) |
| *C07C 2/12* | (2006.01) |
| *C07C 51/06* | (2006.01) |
| *C07C 51/08* | (2006.01) |
| *C07C 51/47* | (2006.01) |
| *C07C 53/08* | (2006.01) |
| *C07C 53/122* | (2006.01) |
| *B01J 20/10* | (2006.01) |

(52) U.S. Cl.
CPC .............. *C07C 7/1485* (2013.01); *B01J 20/06* (2013.01); *B01J 20/08* (2013.01); *B01J 20/103* (2013.01); *B01J 20/12* (2013.01); *B01J 20/186* (2013.01); *B01J 20/20* (2013.01); *B01J 21/04* (2013.01); *B01J 29/70* (2013.01); *C07C 2/12* (2013.01); *C07C 7/005* (2013.01); *C07C 7/12* (2013.01); *C07C 7/148* (2013.01); *C07C 7/14866* (2013.01); *C07C 51/06* (2013.01); *C07C 51/08* (2013.01); *C07C 51/47* (2013.01); *C07C 53/08* (2013.01); *C07C 53/122* (2013.01); *B01J 2220/606* (2013.01); *C07C 2521/04* (2013.01); *C07C 2529/06* (2013.01); *C07C 2529/70* (2013.01)

(58) Field of Classification Search
CPC .......... B01J 20/02; B01J 20/08; B01J 20/12; B01J 20/186; B01J 20/20; B01J 21/04; B01J 29/70; B01J 20/103; B01J 220/606; C07C 2/12; C07C 7/14866; C07C 51/08; C07C 51/47; C07C 53/08; C07C 53/122; C07C 11/02; C07C 11/06; C07C 53/05; C07C 7/005; C07C 7/148; C07C 2529/70; C07C 2521/04; C07C 2529/06
USPC ........................................ 585/518, 824, 868
See application file for complete search history.

(56) References Cited

U.S. PATENT DOCUMENTS

| | | | |
|---|---|---|---|
| 3,062,883 A | 11/1962 | Gilbert et al. | |
| 3,922,217 A | 11/1975 | Cohen et al. | |
| 4,973,790 A | 11/1990 | Beech, Jr. et al. | |
| 5,414,183 A * | 5/1995 | Abrevaya | ........... C07C 7/14841 208/254 R |
| 6,019,887 A | 2/2000 | Ramirez de Agudelo et al. | |
| 2002/0111523 A1 | 8/2002 | Mathys et al. | |
| 2005/0137442 A1 | 6/2005 | Gajda et al. | |
| 2007/0086933 A1 | 4/2007 | Negiz et al. | |
| 2008/0194903 A1 | 8/2008 | Schubert et al. | |

FOREIGN PATENT DOCUMENTS

| | | |
|---|---|---|
| EP | 1 216 978 | 6/2002 |
| WO | WO 02/060842 | 8/2002 |

OTHER PUBLICATIONS

Barbosa, L. A. M. M., "*Theoretical Study of Nitrile Hydrolysis by Solid Acid Catalyst*", Proefschrift grad van doctor, Schuit Institute of Catalysis, Laboratory of Inorganic Chemistry and Catalysis, Eindhoven University of Technology, 184 pp. 2000 (XP002668796).
Beard et al., "*Stereoselective Hydrolysis of Nitriles and Amides Under Mild Conditions Using a Whole Cell Catalyst*", Tetrahedron: Asymmetry, vol. 4, No. 6, pp. 1085-1104, 1993 (XP002668797).
Stepanov et al., "*Interaction of Acetonitrile with Olefins and Alcohols in Zeolite H-ZSM-5: In Situ Solid-State NMR Characterization of the Reaction Products*," Chem. Eur. J. 1997, 3, No. 1, pp. 47-56.

* cited by examiner

*Primary Examiner* — William Cheung
(74) *Attorney, Agent, or Firm* — Darryl M. Tyus

(57) ABSTRACT

A process is described, such process comprising i) contacting a hydrocarbon feed with a heterogeneous catalyst under conditions suitable to hydrolyze nitriles present in the feed to form a nitrile hydrolysis product comprising ammonia, carboxylic acid and carboxylate salts or a mixture thereof; and ii) removing the nitrile hydrolysis product from the feed. In an embodiment, the hydrocarbon feed comprises olefins and is intended for use in an olefin oligomerization process.

15 Claims, No Drawings

PROCESS FOR NITRILE REMOVAL FROM HYDROCARBON FEEDS

CROSS REFERENCE TO RELATED APPLICATIONS

This application is a National Stage Application of International Application No. PCT/EP2012/061364, filed Jun. 14, 2012, the disclosure of which is incorporated by reference in its entirety.

FIELD OF THE INVENTION

The present invention relates to process for removing nitriles from hydrocarbon feeds.

BACKGROUND OF THE INVENTION

The higher olefins oligomerization process converts light olefins, typically, $C_3$ to $C_6$ light olefins, to oligomers (higher olefins), typically such as octenes, nonenes and dodecenes. These higher olefins are then used in the production of various intermediates such as plasticizers, mercaptans, surfactants and solvents. The feedstocks used for the higher olefins oligomerization process come from various sources, such as catalytic crackers and steam crackers. Such feeds are known to contain nitrogen containing compounds, which act as poisons for the catalysts typically used in the higher olefins oligomerization process. The presence of poisons in the feeds has a significant impact on the catalyst life, and thus on the operation and economics of the higher olefins oligomerization process. It is known that acidic catalysts like solid phosphoric acid or zeolites typically used in olefin oligomerization processes are susceptible to poisoning from trace amounts of sulphur-, nitrogen- and oxygen-containing compounds in the feed. Such poisons adsorb on the acidic catalysts, blocking acid sites and pores. This causes enhanced deactivation of the catalyst and shorter catalyst life. Special precautions and feed cleanup is required in case the poison levels are too high.

At present there is no known single process that can quantitatively remove all nitrogen containing poisons, for example amines, amides or nitriles, from olefin feeds useful in the higher olefins oligomerization process to meet required feed quality specifications. Water washing only partially removes nitriles, such as acetonitrile, from certain olefin feeds. Not only is the removal process difficult but it is expensive and generates a lot of waste water.

The interaction of acetonitrile with olefins and alcohols in zeolite H-ZSM-5 is described in Chem. Eur. J. 1997, 3, No. 1 pages 47 to 56 "Interaction of Acetonitrile with Olefins and Alcohols in Zeolite H-ZSM-5: In-Situ Solid-State NMR Characterization of the Reaction Products" Alexander G. Stepanov and Mikhail v. Luzgin.

U.S. Pat. No. 5,414,183 discloses isomerization and etherification reactions. Nitrogen contaminants in the hydrocarbon feed stream are converted to hydrolysis products by contact with an alkaline solution. The hydrolysis is not catalyzed. Residual products in the hydrocarbon phase may be removed by a variety of known means including water washing, stripping and adsorption.

U.S. Pat. No. 4,973,790 discloses a process for oligomerizing $C_2$ to $C_{10}$ olefins obtained by catalytic cracking of heavy crude oil. Feed pretreatment is practiced to remove basic nitrogen compounds present in the light olefin feed with a water wash or guard bed. Where the pretreatment comprises at least two steps, the first step is either a water wash step or contact of feed with a solid bed having an affinity for basic nitrogen. The second step is contact with a zeolitic bed.

U.S. 2005/0137442 relates to a transalkylation process where organic nitrogen compounds, including acetonitrile and propionitrile, are removed from an aromatic feed stream by contacting the stream with an acidic molecular sieve at a temperature of at least 120° C.

US2007/0086933 discloses a transalkylation process for reacting carbon number nine aromatics with toluene to form carbon number eight aromatics such a para-xylene. The process uses an alumina guard bed prior to contacting with a transalkylation catalyst in order to remove chlorides from the aromatic feed.

An efficient process for removing nitrile impurities from hydrocarbon feedstocks would be very beneficial, as it would, among other benefits, allow industrial use of such feeds.

SUMMARY OF THE INVENTION

The present invention provides a process comprising
a. contacting a hydrocarbon feed with a heterogeneous catalyst under conditions suitable to hydrolyze nitriles present in the feed to form a nitrile hydrolysis product comprising ammonia, carboxylic acid and carboxylate salts or a mixture thereof; and
b. removing the nitrile hydrolysis product from the feed.

The heterogeneous catalyst used in step i) may be acidic, in which case it may advantageously be selected from zeolites, metal oxides and mixed metal oxides, resins and supported solid acids like solid phosphoric acid.

Alternatively, the heterogenous catalyst used in step i) may be basic, in which case it may advantageously be selected from hydrotalcites, metal oxides and mixed metal oxides.

Preferably, step i) is carried out at a temperature in the range of 40° C. to 250° C.

Preferably, step ii) may comprise a water wash or a step of contacting the feed with an adsorbent.

Also, in all the above-mentioned embodiments, the nitrile may be composed of a hydrocarbon chain with a cyano group (R—CN); where R typically ranges from 1 to 5. The most common examples are acetonitrile, propionitrile or a mixture thereof.

One of the unique features of the present invention is the combination of the poison conversion step with the converted product removal step to deliver purified hydrocarbon feed. After step ii) the poison concentration in the feed is low enough to reduce catalyst poisoning to an operationally and economically acceptable level for subsequent reactions.

Whilst the background of the present invention has been described in the context of the higher olefins reaction, the solution of the present invention for nitrile removal can also be applied to any other process and for any other hydrocarbon feed where nitriles form a poison problem, for example in aromatics production, olefin isomerizations and alkylations.

In the embodiment where the hydrocarbon feed is intended to be used in an olefin oligomerization process, the hydrocarbon feed comprises olefins, preferably olefins having from 3 to 6 carbon atoms, and more preferably olefins having from 3 to 5 carbon atoms and the process further comprises the step of contacting the feed obtained in step ii) with an olefin oligomerization catalyst under conditions suitable to oligomerize the olefins. Conveniently, the catalyst used for olefin oligomerization is a zeolite, nickel oxide, phosphoric acid, mixtures or combinations thereof.

The process according to the present invention provides an additional degree of flexibility to the higher olefins process for feed selection, as the mechanism converting the nitriles into ammonia is the same for acetonitrile, propionitrile and any other nitrile found in the typical olefin feedstreams (e.g. propene, butenes, pentenes, hexenes). It also makes the higher olefins process less dependent on day to day variations in feed quality, such as upsets upstream introducing ammonia.

DETAILED DESCRIPTION

Hydrocarbon Feed

The hydrocarbon feed according to the present invention can include olefinic, aromatic or aliphatic hydrocarbons or a combination thereof. Whilst the process of the present invention is not limited by hydrocarbon feed or the type of process for which the hydrocarbon is used, preferably the process of the present invention is part of an oligomerization process and the hydrocarbon feed is an olefin feed.

As used herein, "olefins" refers to any unsaturated hydrocarbons having the formula $C_nH_{2n}$, wherein C is a carbon atom, H is a hydrogen atom, and n is the number of carbon atoms in the olefin. According to this invention, the olefins in the feed typically have from 2 to 15 carbon atoms, such as at least 3 and no more than 8 carbon atoms, and typically at least 3 and no more than 6 carbon atoms. They are also referred to as lower olefins. The olefins present in the fees may also be referred to as lower olefins or light olefins.

The feed may also comprise one or more paraffins. As used herein, "paraffins" refers to any of the saturated hydrocarbons having the formula $C_nH_{2n+2}$, wherein C is a carbon atom, H is a hydrogen atom, and n is the number of carbon atoms in the paraffin. The paraffins that may be present in the olefin feed typically have from 1 to 25 carbon atoms, such as from 1 to 15 carbon atoms, and conveniently at least 3 and no more than 6 carbon atoms. Examples of suitable paraffins include methane, ethane, propane, butane, pentane, hexane, isomers thereof and mixtures thereof. If present in the feed, the paraffins may have the same or a different number of carbon atoms as the olefins.

If present, the paraffin acts as a diluent. If used, the olefin feed may comprise at least 10%, at least 25%, at least 30%, at least 35%, or at least 40% paraffin, based upon the total volume of the feed. Alternatively stated, if used, the diluent may be present in the olefin feed in the range from 10% to 40%, alternatively, from 10% to 35%, and alternatively, from 20% to 35% based upon the total volume of the feed. The diluent may also be fed to the reactor(s) separately from the olefin feed. When fed separately, the diluent may be fed in amounts equivalent to those mentioned above, where the diluent is co-fed with the feed. These amounts may not necessarily be the same as the ranges stated above given that more or less of the diluent may be necessary when fed separately to provide an equivalent.

In a class of embodiments, the olefin feed comprises olefins selected from propene, butenes, pentenes, hexenes, their isomers, and mixtures thereof. The process of this invention is especially useful for the oligomerization of feeds comprising propene, butenes, pentenes, their isomers, and mixtures thereof. As used herein, "isomers" refers to compounds having the same molecular formula but different structural formula.

Additionally, the feed may comprise an oligomer (higher olefin), for example, a dimer, such as one provided by recycling a part of an olefin oligomerization product stream. As used herein, "oligomer(s)" or "oligomer product" refers to an olefin (or a mixture of olefins) made from a few light olefins. For example, oligomers include dimers, trimers, tetramers, obtained from two, three or four light olefins of the same number of carbon atoms, mixed oligomers, obtained from 2 or more olefins having different numbers of carbon atoms and mixtures thereof. In a class of embodiments, "oligomer(s)" refers to an olefin (or a mixture of olefins) having 20 carbon atoms or less, alternatively, 15 carbon atoms or less, such as 10 carbon atoms or less, alternatively, 9 carbon atoms or less, and conveniently, 8 carbon atoms or less that has been obtained by linking two or more light olefins together. As used herein, "oligomerization process" refers to any process by which light olefins are linked together to form the oligomer(s) as defined above. As used herein, the term "oligomerization conditions" refers to any and all those variations of equipment, conditions (e.g. temperatures, pressures, weight hourly space velocities etc.), materials, and reactor schemes that are suitable to conduct the oligomerization process to produce the oligomer(s) as known and applied in the art and discussed more below.

In a class of embodiments, the feed comprises 30 wt % or more olefins, such as 40 wt % or more olefins, alternatively, 50 wt % or more olefins, alternatively, 60 wt % or more olefins, alternatively, 70 wt % or more olefins, and alternatively, 80 wt % or more olefins, based upon the total weight of the olefin feed.

In any of the olefin oligomerization embodiments described herein, the feed should be totally free, or at least substantially free, of aromatic hydrocarbon compounds that consist solely of hydrogen and carbon atoms. In this context, "substantially free" means that the olefin feed contains 25 wt % or less, preferably 15 wt % or less, more preferably 10 wt % or less, such as 5 wt % or less, and most preferably 1 wt % or less aromatic hydrocarbon, based upon the total weight of the olefin feed.

Examples of suitable olefin feeds include untreated refinery streams such as Fluidized Catalytic Cracking (FCC) streams, coke streams, pyrolysis gasoline streams or reformates.

Other examples of suitable olefin feeds include refinery feeds often referred to as Raffinate-1 (RAF-1), Raffinate-2 (RAF-2) or Raffinate-3 (RAF-3). Typically, Raffinate-1, Raffinate-2 and Raffinate-3 may be regarded as streams obtainable at various stages in the processing of crude $C_4$ streams obtained from petroleum refining processes. These streams are usually from olefin steam crackers but may also come from refinery catalytic crackers, in which case they generally contain the same components but in different proportions. The first stage of processing these crude $C_4$ refinery streams is to remove butadiene from these streams, such as by solvent extraction or hydrogenation. Butadiene is generally present in the crude $C_4$ refinery streams as 40-45 wt. % of the stream. The product obtained after butadiene removal is Raffinate-1. It generally consists of isobutylene, the two isomers of n-butane, 1-butene and 2-butene, and smaller quantities of butanes and other compounds. The next step consists in removing isobutylene, usually by reaction of isobutylene with methanol to produce methyl-tert-butylether (MTBE), which then produces Raffinate-2. Raffinate-3 (RAF-3) is less common but may be obtained after separation of 1-butene from Raffinate 2. Raffinate-3 typically has a residual 1-butene content of about 1%.

In another embodiment, the feed comprises an FCC light olefin stream that typically comprises ethane, ethylene, propane, propylene, isobutane, n-butane, butenes, pentanes, and other optional components.

According to the present invention, any of the above-described feeds contains organic nitrile contaminants which must be removed to an acceptable level before the hydrocarbon feed undergoes reaction. As used herein, "nitrile" is any organic compound that has a nitrile group (also referred to as a cyano functional group or —C≡N functional group). In the nitrile group, the carbon atom and the nitrogen atom are triple bonded together. As used herein, "acetonitrile" (ACN) is the chemical compound with formula $CH_3CN$. This colorless liquid is the simplest organic nitrile. As used herein, "propanenitrile", "propionitrile", or "ethyl cyanide" is a nitrile with the molecular formula $C_2H_5CN$ and the terms may be used interchangeably. It is also a clear liquid. As used herein, "nitrile" may also refer to heavier nitriles. In the most preferred embodiment the nitrile to be removed is any of acetonitrile or propionitrile. These compounds are especially toxic to oligomerization catalysts and their removal leads to significant catalyst life improvement.

Typically, the nitrile content in the hydrocarbon feed before step i) may be about 3 ppm or more, such as about 5 ppm or more, typically, 10 ppm or more, such as 20 ppm or more, and yet alternatively, 30 ppm or more, calculated on a nitrogen atom basis by weight (wt ppm), with respect to the total weight of hydrocarbon in the stream.

Nitrile Removal Process

The present invention provides a process for removing nitriles from a hydrocarbon feed, in which nitrile removal takes place by contacting the hydrocarbon feed with a heterogeneous catalyst, under conditions suitable to hydrolyze nitriles. The product of hydrolysis comprises any one of ammonia, carboxylic acids, ammonium carboxylates, or a mixture thereof.

The hydrolysis of nitriles in the hydrocarbon feed is catalyzed by a heterogeneous catalyst. Such a catalyst may be acidic or basic. The advantage of using a heterogeneous catalyst is not only that the hydrolysis occurs at a faster rate, but also that problems, such as the requirement for an additional feed pump, corrosion, need for separation from the hydrocarbon feed stream and the such like, are avoided. The hydrolysis can be carried out with or without adding water to the feed.

Examples of acidic heterogeneous catalysts suitable for nitrile hydrolysis according to the invention include zeolites, metal oxides and mixed metal oxides, ion exchange resins and solid phosphoric acid. Non limiting examples of such zeolites include those of the MFI framework type, such as ZSM-5 and zeolite beta, especially those such zeolites having a high silica to alumina ratio, conveniently greater than 200:1, such as 250:1 or 450:1. Such zeolites are also quite useful to remove low molecular weight disulfides, which may also be present as impurities in olefin feedstocks typically used in olefin oligomerization processes. Examples of metal oxides and mixed metal oxides are alumina, silica, silica-alumina, zirconia, or any other oxide that has acidic properties.

Examples of basic heterogeneous catalysts suitable for nitrile hydrolysis according to the invention include hydrotalcites, metal oxides such as MgO, CaO, SrO, and BaO, and mixed metal oxides.

Depending on the type of heterogenous catalyst used, hydrolysis can be carried out at temperatures ranging from room temperature to 400° C. Preferably, the temperature is 40 to 250° C. Pressure can vary from atmospheric to 100 bar. The catalyst acidity, process temperature and pressure can be adjusted such that selective nitrile conversion will occur without concurrent hydrocarbon feed reaction, such as oligomerization in the case of an olefin feed.

The nitriles are fully hydrolyzed to products including any one of ammonia, carboxylic acids and carboxylic acid salts, depending on the initial nitrile. Ammonia can conveniently be removed by a simple water wash. Ammonia may also combine with the carboxylic acid to produce the corresponding ammonium carboxylate, e.g. ammonium acetate, ammonium propionate, which are removed from the hydrocarbon feedstream using the water wash.

The products of nitrile hydrolysis can be removed from the hydrocarbon feedstock by various methods. One method is water wash, which can be carried out by sending the hydrocarbon feed that has undergone nitrile hydrolysis to a water wash tower, where the products of nitrile hydrolysis are removed from the olefin feed by extraction.

Alternatively, removal of the nitrile hydrolysis products from the hydrocarbon feed is carried out by contacting the feed with an adsorbent. This can be carried out at room temperature up to 250° C. Preferably, the feed contacts the adsorbent at temperatures no greater than 40° C. Contacting the feed with an adsorbent traps the products of nitrile hydrolysis and purifies the hydrocarbon feed. The pressure employed during adsorption may be in the range of from about 400 psig to about 4000 psig (2860 kPa to 27688 kPa), and preferably, from about 500 psig to about 1500 psig (3550 kPa to 10446 kPa). The hydrocarbon feed weight hourly space velocity may be in the range of from about 0.1 $hr^{-1}$ to about 20 $hr^{-1}$ or from about 0.5 $hr^{-1}$ to about 5 $hr^{-1}$.

Examples of adsorbents suitable for removing the products of nitrile hydrolysis in the process of the invention include zeolites (acidic, cation-exchanged or metal modified), or non-zeolitic adsorbents, such as alumina (aluminium oxide), preferably gamma or eta alumina, silica, activated carbons, clays, metal oxides and mixed metal oxides. When a zeolite is used to hydrolyze the nitriles, it can also be used at the same time to adsorb the products of nitrile hydrolysis without requiring a separate adsorption step.

Examples of non-zeolitic metal oxides other than alumina include tin oxide, zirconium oxide, titanium oxide, iron oxide, magnesium and tungsten oxide, silicon oxide, copper oxide, nickel oxide, zinc oxide, and mixtures thereof. The adsorbent can comprise two or more of the metal oxides listed above and in any combination. There are different ways to prepare multi metal oxide compositions, including physical mixing and co-precipitation methods.

The zeolitic or non-zeolitic metal oxide or multi metal oxide used as the adsorbent may also contain metals and noble metals added to the metal oxide or multi metal oxide by impregnation or other preparation methods.

The arrangement for the process can also comprise more than one adsorbent having the same or different composition. The presence of more than one adsorbent enables a longer run length and while one or more adsorbents are in use the other(s) can be regenerated. This ensures a continuous process for the removal of converted nitriles and purification of the hydrocarbon feed.

A combination of water wash and adsorption can also be used, whereby the water wash is followed by contact with an adsorbent or vice versa. Such a combination provides a greater flexibility for removal of the products of nitrile hydrolysis depending on the equipment that may be available industrially.

The step of nitrile hydrolysis and the step of removal of the products of nitrile hydrolysis can be carried out in the same vessel or different vessels. The benefit of separate vessels is that there can be independent control of process conditions such as temperature and pressure to ensure optimal rates for both steps. The benefit of being in the same vessel is that the arrangement for the process is more compact and easier to construct.

The process of the present invention can also advantageously comprise the step of removing nitrogen compounds present in the hydrocarbon feed before carrying out the step of nitrile hydrolysis. As a result the hydrocarbon feed can be even further purified not only from nitriles, but also from other nitrogen-containing species which were already present in the feed before the nitrile hydrolysis, such as in particular ammonia, which may interfere with the nitrile hydrolysis.

Following the step of removing the products of nitrile hydrolysis, the nitrile content in the hydrocarbon stream is about 1.50 ppm or less, alternatively, 1.00 ppm or less, such as 0.50 ppm or less, alternatively, 0.30 ppm or less, 0.20 ppm or less, and yet preferably 0.10 ppm or less calculated on a nitrogen atomic basis by weight (wt ppm) relative to the total weight of hydrocarbons in the stream.

Oligomerization

When the process is part of an oligomerization process and the hydrocarbon feed is an olefin feed, the process preferably further comprises after the step of removing the products of nitrile hydrolysis from the feed, a step of contacting the feed with a catalyst under conditions suitable to oligomerize the olefin. In such case, the oligomerization process integrates all steps for oligomerizing a purified olefin feed.

In this embodiment of the invention, once the nitriles in the feed have been hydrolysed and the nitrile hydrolysis products removed, the olefin feed is contacted with a catalyst under conditions suitable to form higher olefins through oligomerization.

One or more catalysts may be used for olefin oligomerization. Any catalyst suitable for olefin oligomerization, whether homogeneous or heterogeneous, may be used, Heterogeneous catalysts may be crystalline or amorphous (non-crystalline) catalysts. Crystalline catalysts include without limitation molecular sieve catalysts such as, for example, zeolite catalysts, in particular, H-zeolites (i.e. zeolites in their proton or acidic form).

Non-crystalline heterogeneous catalysts include without limitation solid acid catalysts such as, for example, solid phosphoric acid (SPA) catalysts and supported metal catalysts or supported metal oxide catalysts. Non-limiting examples of olefin oligomerization processes using such catalysts may be found as follows. Olefin oligomerization using SPA catalysts is disclosed for example in U.S. Pat. No. 6,025,533, WO 92/13818 or WO 2005/058777. The CAT-POLY™ Process (UOP and Süd Chemie) employs phosphoric acid on a silica support. The OCTOL™ Process (UOP/Huels (now Evonik)) employs a nickel containing catalyst on a silica/aluminium oxide support. See *Make plasticizer olefins via n-butene dimerization* R. H. Friedlander et al., Hydrocarbon Processing, February 1986, pages 31-33, and U.S. Pat. No. 5,177,282. Amorphous silica aluminium oxide supports are useful and commonly utilized. Solid acid catalysts may be optionally used with promoters such as $TaF_5$.

In another embodiment, olefin oligomerization can take place in the presence of a homogenous catalyst. Non-limiting examples of such catalysts are provided as follows. The IFP (now Axens) DIMERSOL® processes employs a Ni-based homogeneous catalyst. (Y. Chauvin et al. Chemistry and Industry, 1974, 373-378). U.S. Pat. No. 4,225,743 discloses a homogeneous catalyst system suitable for olefin oligomerization, consisting of a nickel (II) salt of octanoic acid, ethylaluminium dichloride, and a free fatty acid.

Preferably, the catalyst is selected from catalysts comprising a zeolite, nickel oxide or phosphoric acid.

Zeolites are also suitable olefin oligomerization catalysts; they are crystalline heterogenous catalysts. The term "zeolites" is often used to describe the aluminosilicate members of the family of microporous solids known as "molecular sieves". The term molecular sieve refers to a particular property of these materials, i.e., the ability to selectively sort molecules based primarily on a size exclusion process. This is due to a very regular pore structure of molecular dimensions. The maximum size of the molecular or ionic species that can enter the pores of a zeolite is controlled by the dimensions of the channels. These are conventionally defined by the ring size of the aperture, where, for example, the term "8-ring" refers to a closed loop that is built from 8 tetrahedrally coordinated silicon or aluminum atoms and 8 oxygen atoms. These rings are not always perfectly symmetrical due to a variety of effects, including strain induced by the bonding between units that are needed to produce the overall structure, or coordination of some of the oxygen atoms of the rings to cations within the structure. Therefore, the pores in many zeolites may not be cylindrical.

In an embodiment, the zeolite catalyst may include a medium pore size molecular sieve having a Constraint Index of about 1 to about 12. Constraint Index and a method of its determination are described in, for example, U.S. Pat. No. 4,016,218.

Examples zeolites suitable for olefin oligomerization include those of the TON framework type (for example, ZSM-22, ISI-1, Theta-1, Nu-10, and KZ-2), those of the MTT framework type (for example, ZSM-23 and KZ-1), those of the MFI framework type (for example, ZSM-5), those of the MFS framework type (for example, ZSM-57), those of the MEL framework type (for example, ZSM-11), those of the MTW framework type (for example, ZSM-12), those of the EUO framework type (for example, EU-1), those of the AEL framework type (for example, SAPO-11), members of the ferrierite family (for example, ZSM-35) and members of the ZSM-48 family of molecular sieves (for example, ZSM-48). Other examples include zeolites of the MWW family (e.g., MCM-22, MCM-48), zeolites of the MOR framework type, or zeolite beta. As used herein, the term "framework type" is used as described in the Atlas of Zeolite Framework Types, Ch. Baerlocher, L. B. McCuster and D. H. Ohlson, Elsevier 2007.

Preferably, the zeolite is selected from at least one of ZSM-5, ZSM-11, ZSM-12, ZSM-18, ZSM-22, ZSM-23, ZSM-35, ZSM-38, ZSM-48, ZSM-50, zeolites of the MFS framework type, for example ZSM-57, zeolites of the TON framework type, for example ZSM-22, and mixtures thereof.

Mixtures of two or more zeolites may be used in the oligomerization process. For example, the mixture may include ZSM-22 and ZSM-57 or ZSM-22 and ZSM-5 or ZSM-57 and ZSM-5. The zeolite catalyst may also be combined with other types of catalysts such as a solid phosphoric acid (sPa) catalyst.

The zeolite used in the oligomerization catalyst may have an average crystallite or particle size of up to 15 µm, such as within the range of from 0.01 to 6 µm, alternatively, from 0.05 to 5 µm, and alternatively, from 0.1 to 3 µm. As used herein, "average particle size" refers to the arithmetic average of the diameter distribution of the crystals on a volume basis.

Preferably, the zeolite is used in its proton, or acidic form. To obtain this form, an as-synthesized zeolite that has been obtained in an alkaline or alkaline-metal form is advantageously converted to its acid form, for example, by acid treatment, e.g. by HCl, acetic acid, etc. or by ion exchange, for example, ammonium ion exchange. Subsequently, it may undergo calcination before use. The calcined materials may be post-treated, such as by steaming.

Zeolites may be produced by any suitable method known for the given type of zeolite. One technique includes heating a reaction mixture containing a source of silicon oxide, a source of aluminum oxide and, if appropriate, an organic promoter, for example, a nitrogen or phosphorus-containing organic base, together optionally, with an alkali metal base, and separating the porous aluminosilicate crystals (zeolite precursor crystals) formed. The precursor crystals are then calcined in air or oxygen at a temperature exceeding or about 500° C., for example, at a temperature of 550° C. for about 10 to about 20 hours. As recognized in the art, calcination temperatures and durations may vary depending on the type of zeolite catalyst or combination of zeolite catalysts selected. In one embodiment, the calcined material is exchanged with ammonium ions ($NH_4+$) and subjected to conditions under which the ammonium ions decompose, with the formation of ammonia and a proton, thus, producing an acidic form of the at least one zeolite catalyst. Alternatively, the acidic form of the catalyst may be obtained by acid exchange with hydrochloric acid, acetic acid, etc. If desired, however, the calcined material may be used as a catalyst without first being exchanged with ammonium ions, since the material already possesses acidic sites.

Ammonium exchanged and calcined monodimensional 10-rings zeolites (e.g., ZSM-22 and ZSM-23) may be treated to selectivate their surface, thereby, forming a selectivated catalyst. This selectivation may be achieved in numerous ways. In an embodiment, the at least one zeolite catalyst may be titrated with an organic nitrogen base, such as collidine. See, for example, U.S. Pat. No. 5,026,933. Another example is by depositing a crystalline Si:Al layer on a core of zeolite where this layer has a higher Si:Al ratio than the untreated zeolite. See, for example, U.S. Pat. No. 6,013,851.

Although much of the discussion above is directed to aluminosilicate zeolites, it is possible to use material in which silicon and aluminum have been replaced in whole or in part by other elements, for example, any one or more of a Group 2 to Group 15 atom. For example, silicon may be replaced by or contacted with germanium and aluminum or may be replaced with boron, gallium, chromium, and iron. As used herein, these materials containing such replacement lattice elements may also be termed zeolites.

It may be desirable to incorporate the molecular sieves or zeolites mentioned above with another material that is resistant to the temperatures and other conditions employed in the olefin oligomerization process. Thus the molecular sieves or zeolites may be used in the form of an extrudate with binder, where the molecular sieve or zeolite is dispersed within a conventional binder. Binding is typically done by forming a pill, sphere, or extrudate. The extrudate is usually formed by extruding the molecular sieve, optionally in the presence of a binder, and drying and calcining the resulting extrudate. The binder materials used are resistant to the temperatures and other conditions, e.g., mechanical attrition, which occur in various hydrocarbon conversion processes.

Examples of binder materials that may be employed with the molecular sieves or zeolites suitable for use in the process of the invention include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Naturally occurring clays which may be used include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or after being subjected to calcination, acid treatment or chemical modification. Examples of other materials include porous matrix materials such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

Exemplary catalyst materials and processes for making such catalysts may also be found in U.S. Pat. Nos. 3,960,978, 4,016,218, 4,021,502, 4,381,255, 4,560,536, 4,919,896, 5,446,222, 5,672,800, 6,143,942, 6,517,807, 6,884,914, U.S. Patent Application Publication No. 2006/0199987, EP 746 538 A, WO 1994/12452 WO 2005/118512, WO 2005/118513, WO 2007/006398, and WO 2008/088452. See also "Atlas of Zeolite Structure Types," Eds. W. H. Meier, D. H. Olson and Ch. Baerlocher, Elsevier, Fourth Edition, 1996.

In order to carry our olefin oligomerization, the olefin feed with reduced level of nitriles is contacted with a catalyst under conditions suitable to oligomerize the olefins. The olefin oligomerization reaction system may include one or more of a fixed bed reactor, a packed bed reactor, a tubular reactor, a fluidized bed reactor, a slurry reactor, a continuous catalyst regeneration reactor, and any combination thereof. These reactors may be operated in any combination such as, for example, in series and/or parallel sequence. In several embodiments, they may be operated in semi-continuous (i.e., continuous but that can easily be shut down for routine maintenance), continuous, or batch mode.

Oligomerization may be carried out at temperatures from about 80° C. to about 350° C. Close to and above the upper end of the range, cracking increases and may predominate over the oligomerization reaction providing an upper limit to practical operation. More typically, the reaction temperature is from about 130° C. to about 320° C., preferably from about 135° C. to about 310° C., and even more preferably from about 160° C. to about 270° C.

The pressure may be in the range of from about 400 psig to about 4000 psig (2860 kPa to 27688 kPa), and alternatively, from about 500 psig to about 1500 psig (3550 kPa to 10446 kPa).

The olefin weight hourly space velocity based on catalyst, may be in the range of from about 0.1 $hr^{-1}$ to about 20 $hr^{-1}$ or from about 0.5 $hr^{-1}$ to about 5 $hr^{-1}$.

In one embodiment, oligomerization is conducted at a temperature of 80-350° C.; an olefin weight hourly space velocity of 0.1-20 $hr^{-1}$; and a pressure of 2860-27688 kPa.

In another embodiment, the process is conducted at a temperature of 130-320° C.; an olefin weight hourly space velocity of 0.5-5 $hr^{-1}$; and a pressure of 3550-10446 kPa.

Optionally, the olefin feed may also be hydrated (i.e., contacted with water) prior to oligomerization. In an embodiment, sufficient water is used to saturate the feed. In particular, the feed may comprise from about 0.01 to about 0.25, alternatively, from about 0.02 to about 0.20, and alternatively, from about 0.03 to about 0.10, mol % water based on the total hydrocarbon content of the feed. If desired and by way of example, the water content of the feed may be increased by passage through a thermostatted water saturator. The olefin feed used in the oligomerization step can therefore be wet or dry.

In a class of embodiments, the product of oligomerization includes a hydrocarbon composition comprising olefins having at least 6 carbon atoms. Preferably, the product comprises at least 80 wt %, alternatively, at least 90 wt % $C_6$ to $C_{20+}$ olefins, based upon the total weight of the reactor effluent (or based on the final reactor effluent if one or more reactors are utilized) The oligomer (higher olefin) product is useful in many applications and is the starting material for further conversion processes. For example, the oligomer product may be polymerized to produce polyolefins that have application in the plastic industry or polymerized to form synthetic basestocks for lubricants. The oligomer product may undergo hydroformylation and subsequently hydrogenation to produce alcohols. The alcohols may be used in industry such as, for example, solvents, or may be used for the production of detergents/surfactants. The alcohols may further be used in many other areas of industry such as, for example, in the production of esters, such as phthalates, adipates or cyclohexanedicarboxylates, that have application as plasticizers. The oligomer product may also be a blend component for fuels.

Preferred embodiments of the present invention are as follows:

Embodiment 1

In a first step, an olefin feed comprising propene contaminated with acetonitrile is contacted with a bed of ion-exchange resin acting as a heterogeneous catalyst under conditions suitable to hydrolyze acetonitrile. As a result acetonitrile present in the olefin feed is converted to ammonia and acetic acid. In a second step the ammonia and acetic acid present in the propene feed are removed by a water wash. Optionally, a third step may take place in which residual ammonia and acetic acid in the stream can be removed by contacting the feed with an adsorbent which removes ammonia and acetic acid. The propene feed in the final step is sent to a reactor containing a zeolite oligomerization catalyst where oligomerization of the purified olefin feed takes place. The catalyst lasts longer as it does not suffer from the effects of nitrile poisoning.

Embodiment 2

An olefin feed comprising pentene contaminated with propionitrile is contacted with a bed of alumina acting as a heterogeneous catalyst. By contacting the bed of alumina, propionitrile in the feed is hydrolyzed to ammonia and propionic acid. These products are then removed from the olefin feed by contacting the feed with an adsorbent which removes ammonia and propionic acid from the pentene feedstock. Optionally, an additional step may then take place in which residual ammonia and propionic acid present in the propene feed are removed by a water wash. The purified feed is then sent to an oligomerization reactor containing a zeolite oligomerization catalyst, where oligomerization of the purified olefin feed takes place. The catalyst lasts longer because it does not suffer from the effects of nitrile poisoning.

The invention claimed is:

1. A process for removing nitriles from a hydrocarbon feed, the process comprising the steps of:
   i) contacting the hydrocarbon feed without added water with a heterogeneous catalyst under conditions suitable to hydrolyze the nitriles present in the hydrocarbon feed to form a nitrile hydrolysis product comprising any one of ammonia, carboxylic acid and carboxylate salts; and
   ii) removing the nitrile hydrolysis product from the feed.

2. The process according to claim 1, wherein the heterogeneous catalyst used in step i) is acidic.

3. The process according to claim 1, wherein the heterogeneous catalyst used in step i) is selected from zeolites, metal oxides, mixed metal oxides, resins and solid phosphoric acid.

4. The process according to claim 1, wherein the heterogeneous catalyst used in step i) is basic.

5. The process according to claim 1, wherein the heterogeneous catalyst used in step i) is selected from hydrotalcites, metal oxides and mixed metal oxides.

6. The process according to claim 1, wherein step i) is carried out at a temperature in the range of 40° C. to 250° C.

7. The process according to claim 1, wherein step ii) comprises a water wash.

8. The process according to claim 1, wherein step ii) comprises contacting the feed with an adsorbent.

9. The process according to claim 1, wherein the nitrile is acetonitrile, propionitrile or a mixture thereof.

10. The process according to claim 1, wherein the process further comprises removing ammonia present in the hydrocarbon feed before process step i).

11. The process according to claim 1, wherein steps i) and ii) are carried out in separate vessels.

12. The process according to claim 1, wherein the hydrocarbon feed comprises olefins.

13. The process according to claim 12, wherein the process further comprises the step of contacting the feed obtained in step ii) with an olefin oligomerization catalyst under conditions suitable to oligomerize the olefins.

14. The process according to claim 13, wherein the olefins in the hydrocarbon feed has from 3 to 6 carbon atoms.

15. The process according to claim 13, wherein the catalyst used for olefin oligomerization is a zeolite, nickel oxide, phosphoric acid, mixtures or combinations thereof.

* * * * *